(12) United States Patent
Riechers et al.

(10) Patent No.: US 9,377,411 B2
(45) Date of Patent: Jun. 28, 2016

(54) TRANSFLEXION PROBE AND TRANSFLECTIVE SENSOR

(75) Inventors: Daniel Riechers, Regensburg (DE); Christian Grimm, Heilbad Heiligenstadt (DE)

(73) Assignee: SARTORIUS STEDIM BIOTECH GMBH, Goettingen (DE)

( * ) Notice: Subject to any disclaimer, the term of this patent is extended or adjusted under 35 U.S.C. 154(b) by 26 days.

(21) Appl. No.: 14/115,158

(22) PCT Filed: May 5, 2012

(86) PCT No.: PCT/EP2012/001941
§ 371 (c)(1),
(2), (4) Date: Nov. 1, 2013

(87) PCT Pub. No.: WO2012/152422
PCT Pub. Date: Nov. 15, 2012

(65) Prior Publication Data
US 2014/0071453 A1 Mar. 13, 2014

(30) Foreign Application Priority Data

May 10, 2011 (DE) .......................... 10 2011 101 108

(51) Int. Cl.
| | | |
|---|---|---|
| G01N 21/00 | (2006.01) |
| G01N 21/25 | (2006.01) |
| G01J 3/42 | (2006.01) |
| G01N 1/10 | (2006.01) |
| G02B 5/08 | (2006.01) |
| G01N 21/85 | (2006.01) |
| G01N 21/359 | (2014.01) |

(52) U.S. Cl.
CPC ............ *G01N 21/85* (2013.01); *G01N 21/8507* (2013.01); *G01N 21/359* (2013.01); *G01N 2021/8521* (2013.01)

(58) Field of Classification Search
CPC .......................... G01N 21/85; G01N 21/8507
USPC ........... 356/436, 409, 246, 418, 319; 359/838
See application file for complete search history.

(56) References Cited

U.S. PATENT DOCUMENTS

| | | | | |
|---|---|---|---|---|
| 3,740,155 A | * | 6/1973 | Keller | G01N 21/8507 356/246 |
| 4,241,257 A | * | 12/1980 | Koester | 250/235 |
| 5,303,036 A | | 4/1994 | McLachlan et al. | |
| 2002/0103439 A1 | * | 8/2002 | Zeng et al. | 600/476 |
| 2006/0272432 A1 | * | 12/2006 | Belongia | 73/864.63 |
| 2010/0214556 A1 | | 8/2010 | Mannhardt et al. | |

FOREIGN PATENT DOCUMENTS

| | | |
|---|---|---|
| DE | 198 43 553 | 4/2000 |
| DE | 10 2005 025 181 | 12/2006 |
| DE | 10 2006 004 916 | 6/2007 |
| WO | 03/087810 | 10/2003 |

OTHER PUBLICATIONS

Tosi, S. et al.—"Assessment of In-line Near-Infrared Spectroscopy for Continuous Monitoring of Fermentation Processes"—Biotechnol. Prog. 2003, 19, pp. 1816-1821.
International Search Report of Sep. 10, 2012.

* cited by examiner

*Primary Examiner* — Tarifur Chowdhury
*Assistant Examiner* — Sunghee Y Gray
(74) *Attorney, Agent, or Firm* — Gerald E. Hespos; Michael J. Porco; Matthew T. Hespos

(57) ABSTRACT

The invention comprises a transflexion probe for carrying out a transflexion measurement on a liquid located in a vessel, comprising a probe shaft (202) which is provided with a light guide path in its interior and at whose front end face there is arranged an open flow chamber (210) with a reflective plate (218) opposite the front end face of the probe shaft (202). The invention is distinguished by the fact that the probe shaft (202) is designed as a rigid cavity which is sealed at its front end face by a transparent window (206) and has at its rear end a first coupling device (204) for the rigid coupling of a sensor module (100) to the probe shaft (202).

6 Claims, 1 Drawing Sheet

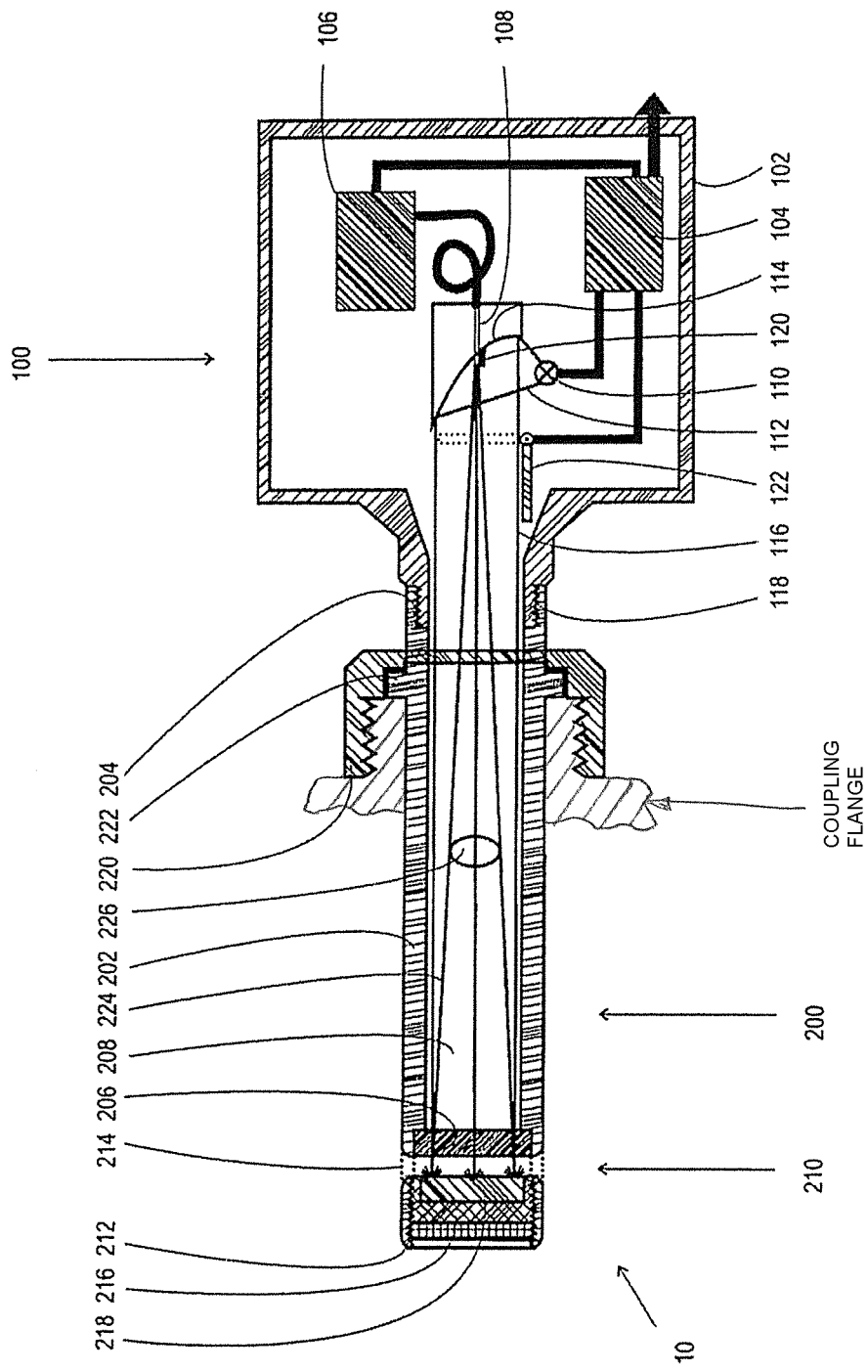

TRANSFLEXION PROBE AND TRANSFLECTIVE SENSOR

BACKGROUND

1. Field of the Invention

The invention relates to a transflexion probe for carrying out a transflexion measurement on a liquid located in a vessel, comprising a probe shaft which is provided with a light guide path in its interior and at whose front end there is arranged an open flow chamber with a reflective plate opposite the front end face of the probe shaft. The invention further relates to a transflective sensor comprising a transflexion probe of the afore-named type and a sensor module coupled thereto.

2. Description of the Related Art

Transflexion probes and transflective sensors are known from Tosi, S. et al.: "Assessment of In-line Near-Infrared Spectroscopy for Continuous Monitoring of Fermentation Processes", Biotechnol. Prog. 2003, 19, 1816-1821. This printed publication describes a sensor based on spectroscopic measurements in the near infrared region for the purpose of monitoring a culture liquid in a bioreactor. The sensor is assembled from a spectrometer unit and a probe which is inserted into the wall of the bioreactor in a way penetrating the latter, makes direct contact at its front end with the culture broth to be monitored, and is coupled at its rear end to the spectrometer unit. The probe comprises an ordered optical fiber bundle which comprises two groups of light guides, specifically a set of annularly arranged, outer illumination fibers, and a set of central detection fibers arranged in the interior of the ring of illumination fibers. A mirrored reflective plate is arranged at an adjustable distance opposite the front end face of said fiber bundle. The mechanical connection between the end face of the fiber bundle and the reflective plate has lateral openings such that the culture broth into which the probe dips with its front end can flow through the interspace between the reflective plate and the end face of the fiber bundle. Said throughflow is promoted by a separate stirring mechanism for circulating the culture broth. At its rear end, the probe is connected via a flexible optical fiber connection to an NIR spectrometer unit. The spectrometer unit comprises a light source whose light is fed into the input of the illumination fibers. Furthermore the spectrometer unit comprises a spectrometer designed for the near infrared region and whose input arrangement is optically coupled to the output of the detection fibers. Light of the light source is fed into the illumination fibers in order to carry out a measurement. Said light emerges at the front end of the optical fiber bundle and radiates through the flow chamber. On the path through the culture broth in the flow chamber, the illuminating light is subject to scattering and/or absorption in accordance with the optical properties of the culture broth. It is reflected at the opposite end of the flow chamber by the reflective plate and once again traverses the flow chamber to impinge again as detecting light on the end face of the fiber bundle. Said component of the detecting light, which impinges within the acceptance angle of the detection fibers, is led back by the latter to the spectrometer unit and coupled via the input arrangement of the spectrometer into the latter such that it is possible to carry out a spectrometric analysis in a known way.

The low measurement sensitivity owing to high optical losses is a disadvantage in the case of the known instrument. In particular, none of the detecting light which impinges on the end face of the fiber bundle outside the small acceptance angle of the detection fibers can be used for measurement. Also, it is particularly the case that the near infrared region is a spectral region of electromagnetic waves which it is difficult to transmit by means of optical fibers. Here, high losses in the fiber material and, in particular, in bends of the fibers occur. Nevertheless, to achieve a sensitive measurement, the light source must be of correspondingly stronger design so as to compensate the losses. However, this leads to an increased energy consumption and to thermal problems in the spectrometer unit.

It is the object of the present invention to develop a transflexion probe and a transflective sensor of the known type in such a way that it is possible to achieve a high sensitivity even with low light output.

SUMMARY OF THE INVENTION

The invention relates to a transflexion probe for carrying out a transflexion measurement on a liquid in a vessel. The transflexion probe has a probe shaft with a front end face, a rear end and an interior defining a rigid cavity between the front end face and the rear end. A light guide path is defined in the interior. An open flow chamber is at the front end face and a reflective plate is opposite the front end face of the probe shaft. The probe shaft is designed as a rigid cavity which is sealed at its front end face by a transparent window and has at its rear end a first coupling device for the rigid coupling of a sensor module to the probe shaft.

Furthermore, said object is achieved by a transflective sensor having the features of claim 6, that is to say by a transflective sensor comprising an inventive transflexion probe and a sensor module which is rigidly coupled to the rear end of the sensor shaft and comprises:

a light source,
an input arrangement of an optical detector,
an illuminating light free beam guiding device, which is set up to direct light of the light source along the longitudinal extent of the sensor shaft to the transparent window, and
a detecting light free beam guiding device which is set up to guide light reflected by the reflective plate through the transparent window to the input arrangement of the optical detector.

Preferred embodiments and developments of the invention are the subject matter of the dependent claims.

The core of the invention is the abandonment of the known fiber optical coupling of transflexion flow cell and actual detector unit. To this end, the fiber bundle is replaced by a preferably cylindrical cavity whose interior offers space for a free beam beam path for feeding illuminating light into the flow chamber and for removing detecting light from the flow chamber. Since the probe shaft thus provided continues to constitute, that is to say to constitute as is known in the prior art, an interface between the vessel interior and the vessel exterior which penetrates the wall of the vessel containing medium to be monitored in the final mounted state, it must at least be ensured that the probe shaft itself is leakproof to the medium. This initially contradicts the idea of the cavity. Consequently, it is provided according to the invention that the probe shaft is sealed at its front end face by a transparent window. In the present context, the term "transparent" means that the window has a transmissivity to light of the respectively required spectral region which suffices for the measurement provided. By way of example, the window can be made from quartz or sapphire in the case of NIR spectroscopy. For other spectral regions and/or other detection methods, the person skilled in the art will know how to undertake a suitable adaptation of the material of the window.

A further difficulty which arises from the free beam guidance in the interior of the hollow probe shaft is that the coupling in and out of the light into and from the probe shaft must always be performed equally. The invention addresses this by providing at the rear end of the probe shaft a first coupling device which permits rigid coupling of the sensor module. For example, it is possible here to provide a thread or a bayonet coupling or similar, a corresponding coupling device needing, of course, to be provided at the input of the sensor module. Here, a module is to be understood as a separate component which has said elements in a fixed spatial relationship to one another. This modular construction also permits the simple and rapid replacement of sensor modules on a probe, or the alternate coupling of a sensor module to different probes on the same or different vessels.

In a preferred development of the invention, it is provided that between its front and its rear ends, the probe shaft has a second, outer coupling device for the rigid coupling, penetrating the vessel wall of the vessel, of the sensor shaft to a corresponding coupling flange of the vessel. Typically, tanks such as are used in the pharmaceutical or biotechnical industry have access ports firmly integrated in the vessel wall. Known port standards are the Ingold port, the Broadly-James port, the B. Braun safety port and others. These have an opening of defined shape and size, and a flange surrounding the opening and having coupling means such as, for example, threads, bayonet couplings, clamping flanges or similar. The shape and size of the inventive probe shaft are advantageously adapted to the respective standard such that the shaft can be introduced with an exact fit into the opening. Furthermore, the shaft preferably has coupling means which correspond to the coupling means of the respective port such that it is possible to produce a tight and secure connection.

As is known in principle from the prior art, the height of the flow chamber can advantageously be set. This means that the optical path which is traversed by illuminating and/or detecting light through the medium to be measured can be set, and thus be adapted to the respective optical conditions of the medium. It is preferred for this purpose to fix the reflective plate on an adjusting plate whose distance from the transparent window can be set by means of a fine thread coupling. This configuration permits the reflective plate, which can be permanently or reversibly connected to the adjusting plate, to be selected in a fashion adapted to the respectively intended measurement. In the context of the present invention, the term "reflective plate" is to be understood in a wide sense, and includes not only reflection purely by optical beams in the manner of a mirror, but also scattering. In particular, it can be provided that the reflective plate exhibits the properties of a Lambert scatterer.

It is preferred to continue the idea of feeding and removing light by free beams in the sensor module to be coupled to the inventive transflexion probe. This means that in the sensor module as well the light is transported completely or at least overwhelmingly as a free beam. It is preferred to provide for this purpose that the illuminating free beam guiding device has a parabolic mirror at whose focal point the light source is arranged. The light of the light source is hereby largely collimated such that it can traverse the length of the probe shaft as far as the flow chamber without substantial losses. In addition, in general terms, the mirror coupling also has the advantage that aberrations, for example, chromatic aberrations such as can be introduced by light guiding means in the form of optical lenses do not occur.

In a preferred development of the present invention, the concept of free beam guidance in the input arrangement of the optical detector is broached. Said detector can be designed straightaway as an optical fiber input. This depends greatly on the nature of the detector. The abovementioned disadvantages of the fiber coupling, which have in particular affected the collection of the detecting light from the flow chamber, no longer occur at this downstream point on the optical path.

Irrespective of the specific nature of the optical measurement, there is frequently the need for a reference measurement with which to compare the actual measurement. In order to enable such a reference measurement it is preferably provided that the sensor module comprises an adjustable reflector unit with the aid of which it is possible in a reference setting to guide light of the light source to the input arrangement of the optical detector. In other words, the adjustable reflector unit, which can, for example, be of foldable design, can, in a first setting, pass light in the way illustrated above, into the transflexion probe and out of the latter, and, in a second setting, backscatter or reflect the light of the light source directly onto the input of the detector. A measurement undertaken in the second position supplies the reference values, while the measurement undertaken in the first position supplies the actual measured values. The reflector unit is preferably configured as a Lambert scatterer, and thus supplies the intensity normal for the determination of the absorbance of the measured substance in the transflexion probe.

Further features and advantages of the invention emerge from the following specific description and the drawings.

BRIEF DESCRIPTION OF THE DRAWINGS

FIG. 1 shows a sectional schematic of an inventive transflective sensor.

DETAILED DESCRIPTION OF THE PREFERRED EMBODIMENTS

FIG. 1 shows a sectional schematic of an inventive transflective sensor 10. The transflective sensor 10 comprises two main units, specifically a sensor module 100 and a transflexion probe 200 which is rigidly coupled at its rear end to the sensor module 100 and is adjoined at its front end by a flow chamber 210.

Inside the housing 102, the sensor module 100 of the embodiment shown has a plurality of units which are not shown in more detail. These are, in particular, a power supply unit 104, which can also be combined with a control unit, and the interface between the sensor module 100 and further units of an installation configured to be as complex as desired. Also shown, purely schematically, is an optical detector 106, which, for example, can be designed as a spectrometer, in particular as an NIR spectrometer, but can also be designed in a different way, for example as a photodiode or as some other type of optical detector. In the embodiment illustrated, the optical input 108 of the optical detector 106 is illustrated as a fiber input. A free beam input can also be implemented in alternative embodiments.

Illustrated in somewhat greater detail is a light source 110, which can be designed, for example, as a tungsten halogen lamp or as a light-emitting diode, in particular with an emission spectrum in the useful wavelength region, for example the NIR region, but can also be designed in a different way, for example, as a gas discharge lamp, laser unit or the like. The light 112 of the light source 110 is collimated by means of a parabolic mirror 114 at whose focal point the light source 110 is arranged. The collimated beam 116 is reflected onto an output opening of the housing 102.

In the embodiment illustrated, said output opening has an external thread 118 onto which the transflexion probe 200— to be explained in more detail below—is screwed. Of course, it is also possible to conceive of other coupling mechanisms at this position such as, for example, a bayonet lock, threaded flanges, clamps, latches, etc.

At the point of intersection of the optical axis, which is defined by the axis of the collimated beam 116, with the contour of the parabolic mirror 114, the latter has a through-opening which is adjoined by the fiber input 108 of the detector 106. On the side of this opening facing the light source 110 there is arranged a narrow diaphragm 120 which prevents a direct incidence of the illuminating light 112 into the fiber input 108. Finally, also included in the housing 102 is an adjustable, preferably foldable reflector unit 122 which, in its position illustrated by continuous lines, does not influence the beam path but which, in its position illustrated by dots, backscatters the beam 116 at least partially onto the fiber input 108.

The sensor module 100 is rigidly connected to the transflexion probe 200—in particular being rigidly screwed in the embodiment shown. The rigidity of the coupling results from the rigidity of the materials selected for said elements, in particular metal or hard plastic.

The transflexion probe 200 comprises a probe shaft 202 which has an essentially hollow cylindrical shape. At its rear end, the probe shaft 202 has an internal thread 204 which corresponds to the external thread 118 of the sensor module 100. At its opposite front end, the probe shaft is sealed by means of an optical window 206 which consists, in particular, of quartz or sapphire. By means of this seal, the hollow interior 208 of the probe 200 and the interior, coupled thereto, of the sensor module 100 are tightly sealed off from the surroundings. Upstream of the optical window 206 is an adjusting ring 212 which is provided with a fine internal thread and is held spaced apart from the optical window 206 by means of webs 214 illustrated by dots. Cutouts are provided between the webs 214. Screwed into the adjusting ring 212 is an adjusting plate 216, which supports, on its side facing the optical window 206, a reflective plate 218 which is designed in particular as a Lambert scatterer. The space between the reflective plate 218 and the optical window 206 acts as a flow chamber 210 because of the webs 214 and the cutouts arranged therebetween. The optical window 206 and the reflective plate 218 are preferably oriented slightly obliquely to one another, that is to say they are at a small angle to one other of approximately 1 to 3 degrees, preferably 2 degrees. Undesired interface reflections are thus prevented.

Finally, near its rear end the transflexion probe has a cap nut 220 which is supported, preferably tightly, against an annular projection 222 and, for the purpose of coupling the probe shaft, can be screwed to a corresponding coupling flange of a vessel (not illustrated).

As described above, in order to carry out a measurement with the aid of the sensor illustrated light 112 of the light source 110 is collimated by means of the mirror 114 and reflected through the output opening of the sensor module 100 into the interior 208 of the probe shaft 202. In this case, the optical axis and the axis of the probe shaft 202 largely coincide. In this way, the light 112 of the light source 110 can be guided largely without losses to the optical window 206 which is transilluminated by it. The flow chamber 210 adjacent to the optical window 206 is also transilluminated. Said flow chamber 210 is flowed through by the medium in the interior of the vessel (not illustrated), such that said medium is likewise transilluminated by the illuminating light 116. At the opposite end, the light is reflected and/or scattered at the reflective plate 218, traverses the flow chamber 210 again, transilluminates the optical window 206 again as detecting light 224, is picked up in the solid angle 226 relative to the numerical aperture of the fiber optic input 108 of the detector 106 and guided to the detector 106 for further measurement. In a specific embodiment, the entire interior 208 of the probe shaft 202 can also be designed as a waveguide by means of reflecting inner surfaces or by the introduction of a transparent optical element, in order to ensure a yet more effective transport of light through the length of the interior 208 of the probe shaft 202.

Of course, the embodiments discussed in the specific description and shown in the figures constitute only illustrative exemplary embodiments of the present invention. In light of the disclosure here, the person skilled in the art is offered a broad spectrum of possible variations. In particular, the dimensions, in particular the length of the probe shaft 202, can be adapted to the respective individual case and the respective vessel size. The medium to be measured which, as a rule, will be liquid, but can also be gaseous, need only have the capability of flowing through the flow chamber 210 between the optical window 206 and the reflective plate 218. It is advantageous to have an intensive throughflow with regard to the representativity of the measurement for the entire vessel interior. The specific dimensioning of the coupling of the inventive sensor to a coupling flange of the vessel is also to be left to the person skilled in the art in view of the individual case.

The invention claimed is:

1. A transflective sensor for carrying out a transflexion measurement on a liquid located in a vessel, comprising:
   a probe shaft (202) having a front end face, a rear end and an interior defining a rigid cavity between the front end face and the rear end, a transparent window (206) sealing the rigid cavity at the front end face of the probe shaft (202) and a first coupling device (204) at the rear end;
   a reflective plate (218) opposed to and spaced from the transparent window (206) at the front end face of the probe shaft (202);
   an open flow chamber (210) between the transparent window (206) and the reflective plate (218); and
   a sensor module (100) rigidly coupled to the first coupling device (204) of the probe shaft (202), the sensor module (100) including:
   an illuminating light guiding device that includes a parabolic mirror (114) with a focal point and a light source (110) arranged at the focal point, the parabolic mirror (114) directing light (112, 116) of the light source (110) along the probe shaft (202) through the transparent window (206) and to the reflective plate (218),
   an optical detector (106) with an input (108),
   a detecting light guiding device set up to guide light (224) reflected by the reflective plate (218) through the transparent window (206) toward the input (108) of the optical detector (106), and
   an adjustable reflector unit (122) that defines a reference setting to guide light (112) from the reflective plate (218) to the input (108) of the optical detector (106), wherein the rigid cavity in the interior of the probe shaft (202) defines a free beam path space forming an optical light guide path along an entire length of the interior between the rear end and the transparent window (206).

2. The transflective sensor of claim 1, wherein the probe shaft (202) has a second coupling device (220, 222) between the front end face and the rear end and for rigidly coupling the probe shaft (202) to a corresponding coupling flange of the vessel while penetrating a vessel wall of the vessel.

3. The transflective sensor of claim 2, wherein the second coupling device (220, 222) is designed to correspond to a coupling flange in accordance with an Ingold, Broadly-James or B. Braun safety port standard.

4. The transflective sensor of claim 1, wherein the reflective plate (218) is fixed on an adjusting plate (216) whose distance from the transparent window (206) can be set by a fine thread coupling.

5. The transflective sensor of claim 1, wherein an inner wall of the probe shaft (202) has a mirrored surface.

6. The transflective sensor of claim 1, wherein the interior of the probe shaft (202) has no optical fibers therein.

* * * * *